United States Patent
C.-Gaudreault

(10) Patent No.: US 6,686,394 B1
(45) Date of Patent: Feb. 3, 2004

(54) ARYL-CHLORO-ETHYL UREAS

(75) Inventor: René C.-Gaudreault, Quebec (CA)

(73) Assignee: Sovar, Societe en Commandite, Sainte-Foy (CA)

(*) Notice: Subject to any disclaimer, the term of this patent is extended or adjusted under 35 U.S.C. 154(b) by 0 days.

(21) Appl. No.: 09/958,786

(22) PCT Filed: Apr. 12, 2000

(86) PCT No.: PCT/CA00/00413
§ 371 (c)(1),
(2), (4) Date: Dec. 6, 2001

(87) PCT Pub. No.: WO00/61546
PCT Pub. Date: Oct. 19, 2000

(30) Foreign Application Priority Data

Apr. 12, 1999 (CA) ............................................. 2268588

(51) Int. Cl.$^7$ ...................... A61K 31/17; C07C 275/28; C07C 275/30
(52) U.S. Cl. .......................... 514/596; 564/48; 564/53; 564/54
(58) Field of Search ............................. 564/53, 48, 54; 514/596

(56) References Cited

U.S. PATENT DOCUMENTS 5,530,026 A   6/1996   Gaudreault et al. ......... 514/524
5,750,547 A   5/1998   Gaudreault et al. ......... 514/346

FOREIGN PATENT DOCUMENTS

EP   0 192 242 A1   8/1986

OTHER PUBLICATIONS

Rohr, O. Chem. Abst. 76:11064 (1972).*
Johnson, "A New Syntheses of 2–Chloroalkyl Isocyanates", *Journal of Organic Chemistry*, vol. 32, pp. 1508–1510, 1967.
Bechard et al. Synthesis and Cytotoxic Activity of New Alkyl [3–(2–choloethyl)ureido] Benzene Derivatives. *European Journal of Medical Chemistry*, vol. 29, pp. 963–966, 1994.
Carmichael. Evaluation of a Tetrazolium–based Semiautomated Colorimetric Assay: Assessment of Chemomsensitivity Testing. *Cancer Research*, vol. 47, pp. 936–942, Feb. 15, 1987.

* cited by examiner

Primary Examiner—Peter O'Sullivan
(74) Attorney, Agent, or Firm—Merchant & Gould P.C.

(57) ABSTRACT

Described herein are novel 1-aryl-3-(2-chloroalkanylureas derivatives. These derivatives are useful anticaner agents having excellent specifilty towards cell targets and potent antineoplastic activity without systemic toxicity derivatives mutagenicity. More specifically, the invention is directed to novel derivatives of the following formula:

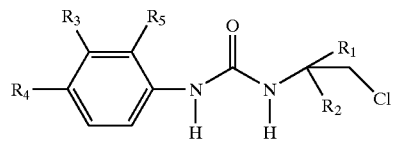

wherein $R_1$ is $C_1$–$C_6$ alkyl, $C_3$–$C_7$ cycloalkyl, $C_1$–$C_6$ alkoxy, $C_1$–$C_6$ hydroxy alkyl, or $C_1$–$C_6$ halide;

$R_2$ is H, $C_1$–$C_6$ alky, $C_3$–$C_7$ cycloalkyl, $C_1$–$C_6$ I alkoxy, $C_1$–$C_6$ hydroxy alkyl or $C_1$–$C_6$ halide, di-halide or tri-halide; $R_1$ and $R_2$ may also be part of cyclic structures.

$R_3$ and $R_4$ are as defined in $R_6$ or, halide, di-halide, tri-halide, $C_1$–$C_7$ lower dialkyl, or alicyclic groups fused to the phenyl ring, these alicyclic ring can be substituted by one or more groups as defined in $R_6$;

or polycyclic rings bearing not more than three rings wherein the rings other than the ring bearing the substituted 2-chloroethylamino moiety can be substituted by one or more groups as defined in $R_6$;

$R_6$ is H, $C_1$–$C_7$ alkyl, $C_1$–$C_7$ alkoxy alkyl, $C_1$–$C_7$ amino alkyl, $C_1$–$C_6$ thio alkyl, $C_1$–$C_5$ S-alkyl, $C_1$–$C_7$ N-alkyl, $C_1$–$C_7$ N,N-dialkyl, $C_1$–$C_7$ cyanoalkyl, $C_1$–$C_7$ haloalkyl, $C_1$–$C_7$ sulfoxide or $C_3$–$C_7$ cycloalkyl; or a prodrug thereof Also disclosed are pharmaceutical compositions containing the compounds of the invention in conjunction with a pharmaceutically acceptable carrier and the use of the compositions in treating cancer.

4 Claims, No Drawings

ARYL-CHLORO-ETHYL UREAS

This application is a 371 of PCT/CA00/00413 filed Apr. 12, 2000.

BACKGROUND OF THE INVENTION

1. Field of Invention

This invention relates to novel anticancer agents having potent antineoplastic activity without systemic toxicity or mutagenicity. Moreover, the compounds of the present invention present higher specificity to cancer cell targets than previously known compounds. The present invention also relates to pharmaceutical compositions comprising at least one compound of the present invention as active agent. More specifically, the invention is directed to novel derivatives of 1-aryl-3-(2-chloroalkanyl)ureas having substituents on the first carbon atom of the 2-chloroalkanyl moeity.

2. The Prior Art

Some 1-aryl-3-(2-chloroalkanyl)urea derivatives (hereinafter referred to as "CAUs") are known from U.S. Pat. Nos. 5,530,026 and 5,750,547 to the same assignee as the present application. More specifically, compounds of the following formula are known:

[Structure: R-substituted phenyl-NH-C(=O)-NH-CH$_2$CH$_2$Cl]

wherein R refers to various substituents on the phenyl ring.

It is known that CAUs display an affinity towards cancer cells, permeate the cell wall and provide a mild alkylating effect on cell components thereby killing the offending cell.

An object of the invention is to provide novel CAU derivatives having significantly superior antineoplastic activity over known CAUs while maintaining low systemic toxicity, mutagenicity and side-effects.

SUMMARY OF THE INVENTION

It has now been found, against expectations and documented precedents that specific substitutions on the first carbon atom of the 2-chloroalkanyl group of the CAU molecule provides a significant improvement on the anticancer effect of the resulting CAU.

Moreover, it has been found that yet unknown substitutions on the phenyl ring render the resulting CAU molecule even more efficient at targeting specific regions of cancerous cells thereby improving their specificity toward various cellular proteins key to cell survival.

More specifically, this invention provides a novel class of CAU derivatives. This novel class of CAU may be expressed by the following formula:

[Structure: phenyl ring with R$_3$, R$_4$, R$_5$ substituents, -NH-C(=O)-NH-C(R$_1$)(R$_2$)-CH$_2$Cl]

wherein $R_1$ is H, $C_1$–$C_6$ alkyl, $C_3$–$C_7$ cycloalkyl, $C_1$–$C_6$ alkoxy, $C_1$–$C_6$ hydroxy alkyl, $C_1$–$C_6$ halide, $C_1$–$C_6$ halo substituted $C_1$–$C_6$ alkyl, halo di-substituted $C_1$–$C_6$ alkyl or halo tri-substituted $C_1$–$C_6$ alkyl;

$R_2$ is $C_1$–$C_6$ alkyl, $C_3$–$C_7$ cycloalkyl, $C_1$–$C_6$ alkoxy, $C_1$–$C_6$ hydroxy alkyl, $C_1$–$C_6$ halide, $C_1$–$C_6$ halo substituted $C_1$–$C_6$ alkyl, halo di-substituted $C_1$–$C_6$ alkyl or halo tri-substituted $C_1$–$C_6$ alkyl;

$R_1$ and $R_2$ could also be part of cyclic structures expressed by the formula: examples:

[Structures: phenyl-NH-C(=O)-NH-cyclobutyl-Cl; phenyl-NH-C(=O)-NH-cyclohexyl-Cl; phenyl-NH-C(=O)-NH-cyclopropyl-(CH$_2$)$_n$-Cl]

n = 1 to 6

$R_3$ and $R_4$ are as defined in $R_6$, or halide, dihalide or trihalide (e.g. $CF_3$) lower dialkyl (1 to 8 carbon atoms) in $R_3$ and $R_4$, (the number of carbon atoms present is not necessarily identical ("asymetric molecules"), or alicyclic groups of the following structures

[Structure: bicyclic indane-type structure with R$_5$ and urea linkage]

wherein n=1 to 3 carbon atoms,

The alicyclic ring could also be substituted by one or more substituting groups comprising groups as described for $R_6$ $R_3$ and $R_4$ can also be polycyclic rings bearing not more than three rings such as dihydrophenanthrene, anthracene, phenanthrene, fluorenyl, etc., examples:

[Structures: benzocyclobutene-urea-CH$_2$CH$_2$Cl; indane-urea-CH$_2$CH$_2$Cl; benzocycloheptane-urea-CH$_2$CH$_2$Cl]

wherein the rings other than the ring bearing the substituted 2-chloroethylamino moiety can be substituted by one or more groups as defined in $R_6$.

$R_5$ is H and $R_6$ lower alkyl (1 to 7 carbon atoms) or
lower alkoxy or hydroxy alkyl, amino alkyl, thio alkyl
   (1 to 7 carbon atoms) or
S-lower alkyl
N-lower alkyl
N,N-dilower alkyl
lower cyanoalkyl (1 to 7 carbon atoms)
cycloalkyl (3 to 7 carbons atoms)
lower haloalkyls (Br, I, Cl, F) (1 to 7 carbon atoms)
lower sulfoxides (1 to 7 carbon atoms)

Further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DETAILED DESCRIPTION OF PREFERRED EMBODIMENTS

Before describing the present invention in detail, it is to be understood that the invention is not limited in its application to the details of the preferred embodiments and examples described herein. The invention is capable of other embodiments and of being practised in various ways. It is also to be understood that the phraseology or terminology used herein is for the purpose of description and not limitation.

Modification of the 2-Chlroalkanyl Moiety ($R_1$ and $R_2$ Groups)

Experiments to assess the biopharmaceutical properties of known 1-aryl-3-(2-chloroethyl) ureas (CAUs) have unexpectedly revealed that certain cell enzymes such as cytochromes $P_{450}$ 1A2 and 2E1 were oxidizing CAUs therefore metabolizing them to inert molecules and depriving them of anticancer effect. The metabolization mechanism was again unexpectedly found to operate on the first carbon atom on the chloro-2-alkenyl moiety adjacent to the urea moiety.

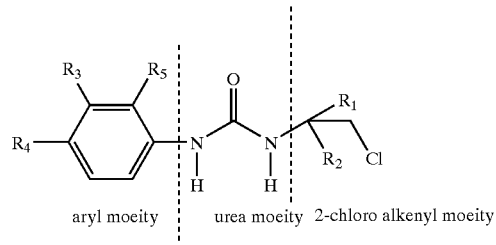

For example, in the case of a 4-tert-butyl CAU (tBCAU), metabolization occurred along the following pathway:

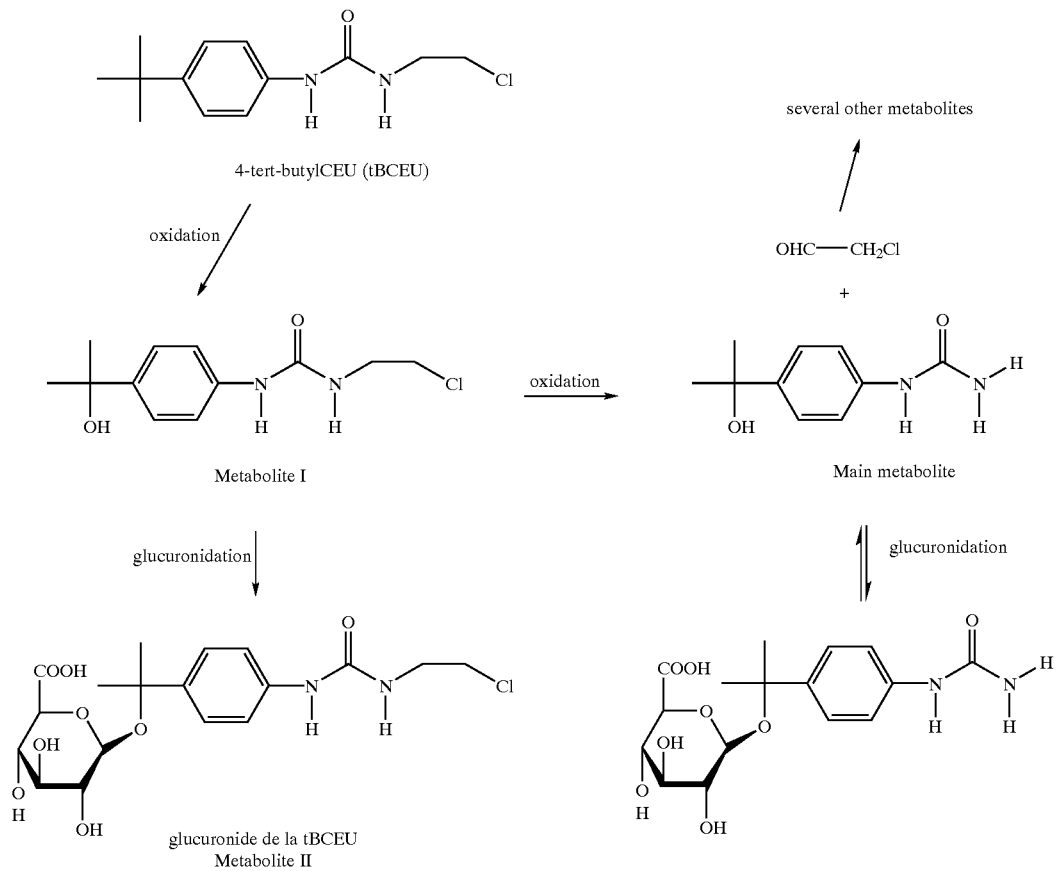

Surprisingly this has revealed a metabolic weak spot at the first carbon atom of the 2-chloro-alkanyl moiety of the CAUs. Thus, the present invention generally aims at providing protecting groups on this first carbon atom and at providing novel CAU derivatives having potent antineoplastic activity.

More specifically, the protection of the weak carbon atom from metabolization was achieved by substituting the hydrogen atoms with groups such as lower alkyl groups such as methyl, ethyl and propyl.

Modification of the $R_3$, $R_4$ and $R_5$ Moieties

Furthermore, it was surprisingly discovered that certain modifications of substituents on the aryl moiety dramatically improved the specificity of the resulting CAU derivatives toward various cellular proteins key to cell survival.

Thus, the following compounds were developed and are expressed by the general formula:

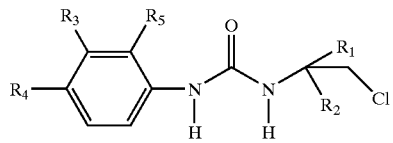

Wherein
$R_1$ is H, $C_1$–$C_6$ alkyl, $C_3$–$C_7$ cycloalkyl, $C_1$–$C_6$ alkoxy, $C_1$–$C_6$ hydroxy alkyl, $C_1$–$C_6$ halide $C_1$–$C_6$ halo substituted $C_1$–$C_6$ alkyl, halo di-substituted $C_1$–$C_6$ alkyl or halo tri-substituted $C_1$–$C_6$ alkyl;

$R_2$ is $C_1$–$C_6$ alkyl, $C_3$–$C_7$ cycloalkyl, $C_1$–$C_6$ alkoxy, $C_1$–$C_6$ hydroxy alkyl $C_1$–$C_6$ halide, $C_1$–$C_6$ halo substituted $C_1$–$C_6$ alkyl, halo di-substituted $C_1$–$C_6$ alkyl or halo tri-substituted $C_1$–$C_6$ alkyl;

$R_1$ and $R_2$ can be part of cyclic structures expressed by the formula:

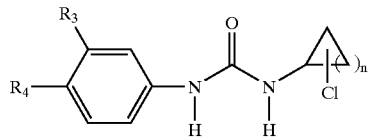

wherein n=1 to 6, such as:

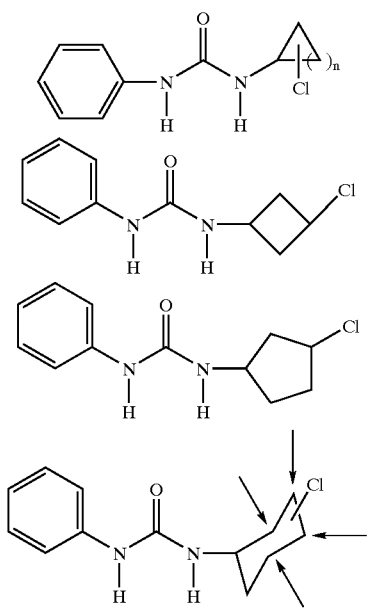

wherein the arrows on the molecule on the right hand side indicate the position where the molecule can be substituted by the chlorine atom;

$R_3$ and $R_4$ are as defined in $R_5$ or halide, dihalide or trihalide (e.g. $CF_3$) lower dialkyl (1 to 8 carbon atoms)

in $R_3$ and $R_4$, (the number of carbon atoms present is not necessarily identical ("asymmetric molecules")) or alicyclic groups of the following structures

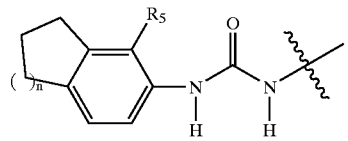

wherein n=1 to 3 carbon atoms ($R_5$ is shown to clearly convey that the fused alicyclic group is fused at the 3 and 4 positions on the phenyl ring, $R_3$ and $R_4$ can also be polycyclic ring systems bearing not more than three rings such as dihydrophenanthrene, dihydroanthracene, anthracene, phenanthrene, fluorenyl, etc., examples:

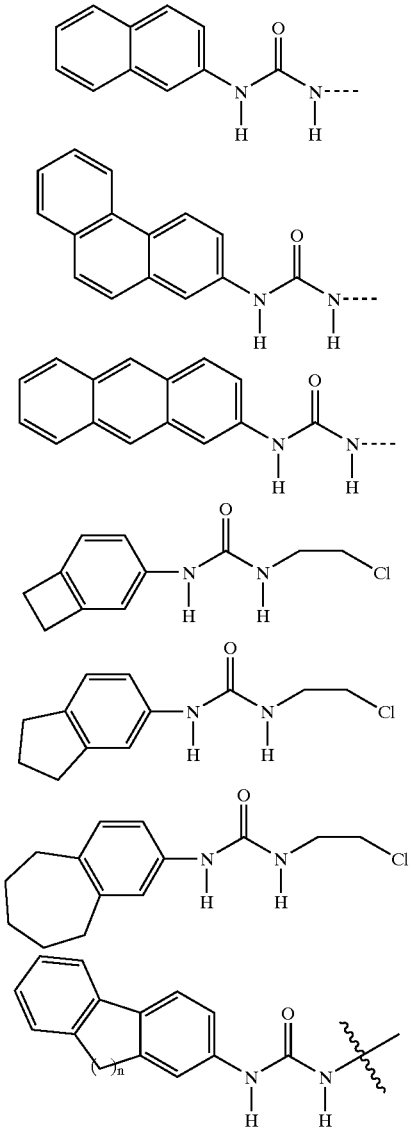

7

-continued n = 1–3 wherein the rings other than the ring bearing the substituted 2-chloroethylamino moiety can be substituted by one or more groups as defined in $R_6$.

$R_5$ is H $R_6$ lower alkyl (1 to 7 carbon atoms) or
lower alkoxy or hydroxy alkyl amino alkyl, thio alkyl (1 to 7 carbon atoms) or
S-lower alkyl
N-lower alkyl
N,N-dilower alkyl
lower cyanoalkyl (1 to 7 carbon atoms)
cycloalkyl (3 to 7 carbons atoms)
lower haloalkyls (Br, I, Cl, F) (1 to 7 carbon atoms)
lower sulfoxides (1 to 7 carbon atoms)

8

β-tubulin has been highly conserved throughout evolution and is therefore present many mammalian cells. Consequently, the compounds of the invention are indicated for: wideranging anticancer agents, transdermic for pre-surgical treatment of melanomas and systemic for other cancers.

Prodrugs of the compounds of the present invention may also be easily prepared. As an example of prodrugs of the compounds of the present invention, the sulfone and sulfoxide derivatives of alkylthio substituents is immediately contemplated by skilled worker in this art. The sulfone and sulfoxide derivatives while not generally active will be activated once administered to a patient. The activation will occur when the prodrug is reduced to yield the corresponding alkylthio, an active compound.

The following synthesis flowsheet illustrates one route of preparation of CAU derivatives of the present invention.

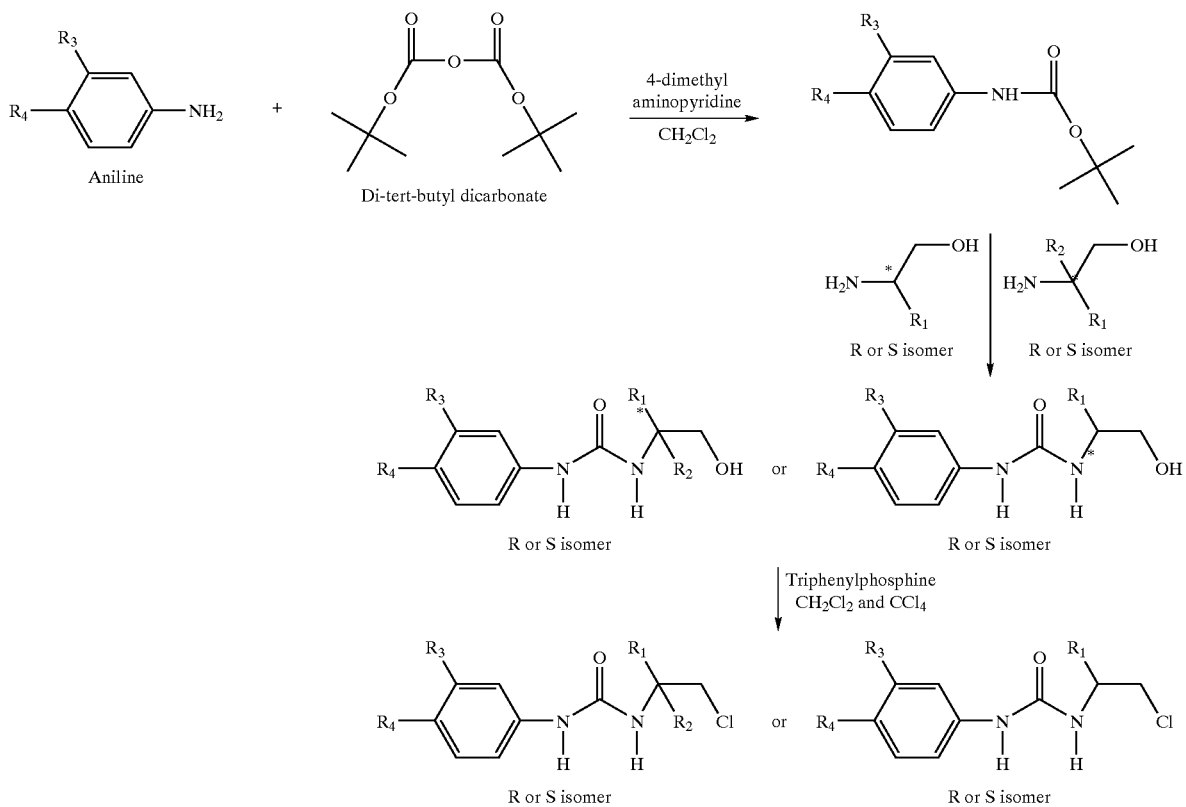

Preparation of CAU Derivatives

The compounds of the present invention are easily prepared in good yields without concomitant polymerization or decomposition. The compounds are also easily purified by usual techniques such as crystallization or liquid chromatography. Furthermore, the compounds exhibit an extended shelf life without decomposition in air.

The type and level of activity for a given dosage of each compound can be conventionally determined by routine experimentation using well-known pharmacological protocols.

The compounds of the present invention appear to kill cancer tumor cells by alkylation of their β-tubulin on a specific cysteine residue (Cyst-239) and also by other mechanisms under investigation. The molecular structure of It is important to note that the preparation of CAU derivatives of the present invention has led to the formation of R and S isomers which (in some cases) exhibit significant differences in cytotoxic activities (see Tables I and II below).

EXAMPLES

Preparation of N-(4-Alkylphenyl)-N'-(1-alkyl-2-hydroxy)ethylureas

These compounds were prepared following the general synthetic route illustrated above.

To a stirred solution of di-tert-butyldicarbonate (3.9 mmol) and 4-dimethylaminopyridine (0.4 mmol) in anhydrous dichloromethane (20 mL) was added dropwise the relevant aniline (also 2-aminofluorenyl, 2-aminonaphthyl, etc. derivatives) (3.7 mmol). The reaction mixture was stirred for 30 min at room temperature and the required (R) or (S) aminoalcohol was added dropwise. The mixture was stirred overnight at room temperature. The solvent was evaporated under vacuum and the crude product was purified by flash chromatography on silica gel (dichloromethane/ethyl acetate, 20/80) to yield the hydroxyurea as a colorless solid.

Halogenation of N-(4-Alkylphenyl)-N'-(1-alkyl-2-hydroxy)ethylureas into N-(4-Alkylphenyl)-N'-(1-alkyl-2-chloro)ethylureas A solution of the relevant hydroxyurea (2.4 mmol) and triphenylphosphine (3.7 mmol) in a mixture of dichloromethane and carbon tetrachloride (20:6) was stirred overnight at room temperature. The solvent was evaporated under reduced pressure and the crude product purified by flash chromatography on silica gel (ethylether/petroleum ether, 50/50) to give the chloroethylurea as a white solid.

Of import, the $R_1$ or/and $R_2$ substituted CAUs may also be prepared by several synthetic routes. One skilled in the art will quickly appreciate this.

Example 1

Evaluation of Cytotoxic Activity

Compounds prepared in accordance with the method outlined above were synthesized and evaluated for cytotoxic activity. The molecular structure of each one of them was verified by IR, NMR and mass spectroscopy.

Table I below, provides the evaluation of the in-vitro cytotoxic activities of various compounds prepared in accordance with the synthesis illustrated above and in which $R_3$ and $R_5$ were H.

The conventional evaluation method proposed by the American National Cancer Institute was used. The method measures effectiveness of an anti-cancer drug based on $IC_{50}$ which symbolizes the drug concentration in $\mu$M at which the drug achieves the inhibition of proliferation of a given line of cancer cells by a factor of one half when compared to the normal proliferation of the same line of cancer cells in the same growth media Cytotoxicity Assay:

CAU were tested on several cell lines including human non-hormone-dependant breast cancer cells (MDA-MB-231), and mouse leukemia (L1210). MDA-MB-231. These cell lines were obtained from the American Type Culture Collection (Bethesda, Md., USA). Cytotoxicity of CAU derivatives was tested and compared to the effect of chlorambucil and carmustine.

Tumor cells were grown in RPMI-1640 medium supplemented with 10% fetal calf serum, 2 mM glutamine and 64 U/mL of gentamycin. Cells were routinely passaged at 90% confluence.

Five thousand cells (100 $\mu$l) were seeded in 96 well's plate and incubated for one day at 37° C. under a humidified atmosphere, in presence of 5% $CO_2$. Subsequently, 100 $\mu$l of fresh medium containing CAU to obtain final concentrations ranging from 1- to 200 $\mu$M were added to the cultures. CAU were dissolved in dimethyl sulfoxide (DMSO; Aldrich Chemicals Company Inc., Milwaukee, Wis.) which is maintained at 0.5% (v/v). Cells were incubated for four to five days in the presence of drugs.

Cell's survival was evaluated by colorimetric assay using MTT, according to a modification of the procedure reported by Carmichael and coil. [Carmichael J, De Graff W G, Gazdar A F, Minna I D, Mitchell J B (1987) Cancer Res 47, 936–942]. Briefly, the culture media was replaced by 50 $\mu$l of a solution containing MTT (1.0 mg/ml in PBS: RPMI-1640, (1:4)). The MTT is reduced by mitochondrial dehydrogenase to form MTT-formazan. After two hours of incubation at 37° C., the wells were washed with 200 $\mu$l of saline and 100 $\mu$L of DMSO containing 0.5% v/v of a glycine solution 0.1 M at pH 11 (NaOH) were added to dissolve the precipitate. The plates were then shaken for 15 minutes and the absorbance read at 570 nm with a Behring Elisa Procesor II (Behring, Marburg, Germany).

The evaluation was performed on two typical cancer cell lines namely, L1210 (mouse leukemia cells) and MDA-MB-231(human breast cancer cells). A comparison with conventional anti-cancer drugs chlorambucil and carmustine is provided to illustrate the effectiveness of the compounds of the present invention.

TABLE I

| IN-VITRO CYTOTOXIC ACTIVITY | | | | | |
|---|---|---|---|---|---|
| $IC_{50}$ L1210 ($\mu$M) | $IC_{50}$ MDA-MB-231 ($\mu$M) | $R_1$ | $R_2$ | $R_3$ | $R_4$ |
| 1.3 | 3.1 | H | H | H | sec-butyl |
| 2.0 | 4.5 | * R-methyl | H | H | sec-butyl |
| 19.6 | 72.4 | H | S-methyl | H | sec-butyl |
| 17 | 56 | R-ethyl | H | H | sec-butyl |
| 20.7 | 67 | H | S-ethyl | H | sec-butyl |
| 14 | 32 | R and * S-propyl | H | H | sec-butyl |
| 15 | Nd | Methyl | Methyl | H | sec-butyl |
| 2.6 | 6.2 | H | H | H | tert-butyl |
| 2.3 | 6.1 | R-methyl | H | H | tert-butyl |
| 20 | 74 | H | S-methyl | H | tert-butyl |
| 19 | 55 | R-ethyl | H | H | tert-butyl |
| 16 | 67 | H | S-ethyl | H | tert-butyl |
| 23 | 52 | R and S-propyl | H | H | tert-butyl |
| >100 | >100 | Methyl | Methyl | H | tert-butyl |
| 1.2 | 2.5 | H | H | H | iso-propyl |
| 0.5 | 1.7 | R-methyl | H | H | iso-propyl |
| 29.7 | >100 | H | S-methyl | H | iso-propyl |
| 16 | 49 | R-ethyl | H | H | iso-propyl |
| 22 | 85 | H | S-ethyl | H | iso-propyl |
| 8.7 | 24 | R and S-propyl | H | H | iso-propyl |
| 80 | >100 | Methyl | Methyl | H | iso-propyl |
| 4.5 | 6.8 | Carmustine | | | |
| 2.6 | 81 | Chlorambucil | | | |

Note:*S and *R refer to the isomer form of the carbon to which both R1 and R2 are attached.

The above experiments show that the R isomer on the $R_1$ group provided greater activity than the S isomer.

Example 2

In a related set of experiments, the tert-butyl group of R4 was replaced with iodine to yield 4-iodoCAUs (bioisosteric form of the tert-butyl group). $R_5$ remained H. Table II below evaluates the cytotoxicity of such molecules and the effect of substitution on the 2-chloroethylamino moiety. During the experiments, $IC_{50}$ was recorded against cancer cell lines L1210 and K562 (mouse leukemia cells).

TABLE II

| IN-VITRO CYTOTOXIC ACTIVITY | | | | | |
|---|---|---|---|---|---|
| $IC_{50}$ L1210 ($\mu$M) | $IC_{50}$ K562 ($\mu$M) | $R_1$ | $R_2$ | $R_3$ | $R_4$ |
| 5.4 | 3.8 | H | H | H | I |
| 1.6 | 1.1 | * R-methyl | H | H | I |
| 10 | 7 | H | * S-methyl | H | I |

Note:*S and *R refer to the isomer form of the carbon to which both R1 and R2 are attached.

This table shows that the R isomer of the 4-iodoCAUs (bioisosteric form of the tert-butyl group) following a substitution on the 2-chloroethylamino moiety results in a very active drug.

Example 3

In another related set of experiments wherein $R_1$ is H or $CH_3$, and $R_2$ is $CH_3$, the effect on substitutions on the phenyl ring were observed. It is theorized that theses substitutions assist in the positioning and selectivity of the compounds towards key intracellular proteins.

The results of in-vitro tests are reported in Table III below.

TABLE III

IN-VITRO CYTOTOXIC ACTIVITY

| $R_3$ | $R_4$ | $R_5$ | $IC_{50}$ ($\mu$M) (MDA-MB-231) | $IC_{50}$ ($\mu$M) L1210 |
|---|---|---|---|---|
| H | Methyl | H | 24.1 | 16.4 |
| Methyl | H | H | 60 | 27 |
| Methyl | Methyl | H | 7.2 | 3.8 |
| Methyl | H | Methyl | 20 | 8.8 |

From these observations, the R and S alkyl CAU deriving from 3,4 dimethylCAUs are particularly effective anti-cancer agents.

Example 4

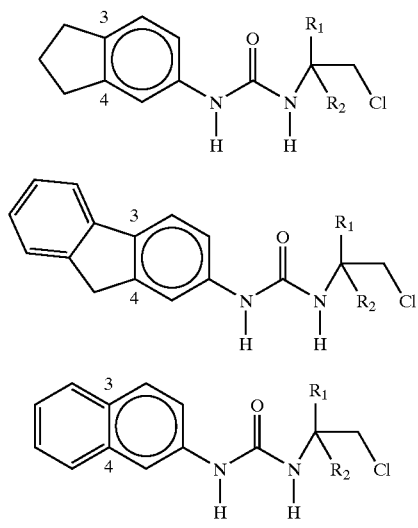

Ceu 1
Ceu 2
Ceu 3

In another experiment the following polycyclic molecules were prepared: wherein $R_1$ is H or $CH_3$, and $R_2$ is $CH_3$ In-vitro cytotoxic activities are reported in Table IV below.

TABLE IV

IN-VITRO CYTOTOXIC ACTIVITY

| DRUG | $R_1$ | $R_2$ | $IC_{50}$ ($\mu$M) CHO | $IC_{50}$ ($\mu$M) MDA-MB-231 |
|---|---|---|---|---|
| CAU-1 | H | H | 9.9 | 10.3 |
| CAU-1 | *R-methyl | H | 9.8 | 9.5 |
| CAU-1 |  | *S-methyl | 78 | >100 |
| CAU-2 | H | H | 9.3 | 9.0 |
| CAU-2 | R-methyl | H | 16.3 | 13 |
| CAU-2 | H | S-methyl | 16.1 | 50 |
| CAU-3 | H | H | 7.2 | 6.1 |
| CAU-3 | R-methyl | H | 3.1 | 3.2 |
| CAU-3 | H | S-methyl | 63 | >100 |

Note:*S and *R refer to the isomer form of the carbon to which both R1 and R2 are attached.

These results show that the modification of the carbon 1' of CAU led to R and S isomers of CAU. R isomers are in most cases more cytotoxic than the unsubstituted CAU. Furthermore, R isomers are in most cases several fold more potent than the S isomers. This might be due to better specificity toward the protein(s) they alkylate.

Example 5

The following compounds were successfully tested for cytotoxic acitivity.

| $R_1$ | $R_2$ | $R_5$ | $IC_{50}$ ($\mu$M) CHO | $IC_{50}$ ($\mu$M) HT-29 | $IC_{50}$ ($\mu$M) K562 | $IC_{50}$ ($\mu$M) MDA-MB-231 |
|---|---|---|---|---|---|---|
| H | * R-ethyl | tert-butyl | 44 | 25 | 32.2 | 55 |
| H | R-ethyl | iso-propyl | 48 | 30 | 18 | 49 |
| H | R-ethyl | sec-butyl | 38 | 27 | 23 | 56 |
| H | R-propyl | tert-butyl | 60 | 27 | 21 | 52 |
| H | R-propyl | iso-propyl | 21.3 | 17 | 6 | 24 |
| H | R-propyl | sec-butyl | 29 | 16.4 | 11 | 32 |

CHO=Chinese Hamster Ovary

MDA-MB-231 Hormone-independant breast cancer

HT-29 human colon carcinoma

K562 human leukemia

Note:*R refers to the R-isomer form of the carbon to which both R1 and R2 are attached.

Examples 6–15

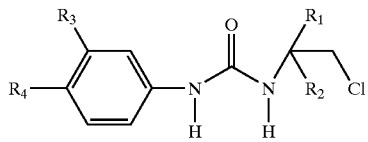

Based on the formula of the compounds of the present invention as shown above, specific molecules were synthesized and later tested for citotoxic activity.

Example 6

| $R_1$ | $R_2$ | $R_3$ | $R_4$ |
|---|---|---|---|
| H | Methyl (S isomer) | H | n-hexyl |

-continued

| R₁ | R₂ | R₃ | R₄ |
|----|----|----|----|

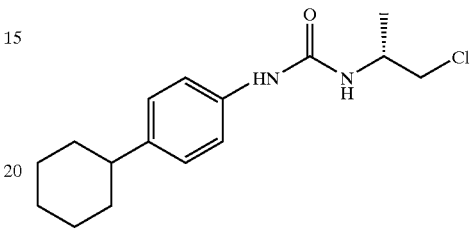

Flash chromatography:ether:petrol ether=1:1; $R_f$=0.31 (ether:petrol ether=1:1); ¹H-NMR (CDCl₃): 7.17 (d, 2H, H-C2 and H-C6, J=8.4 Hz), 7.11 (d, 2H, H-C3 and H-C5, J=8.4 Hz), 4.27 (m, 1H, CH(CH₃)CH₂Cl), 3.72 (dd, 1H, CH₂Cl, J=4.3 and J=11.0 Hz), 3.57 (dd, 1H, CH₂Cl, J=3.4 and J=11.0 Hz), 2.55 (t, 2H, CH₃(CH₂)₄CH₂), 1.53 (m, 2H, CH₃(CH₂)₃CH₂CH₂), 1.23 (d, 3H, CH(CH₃)CH₂Cl, J=6.9 Hz), 1.18–1.43 (m, 6H, CH₃(CH₂)₃CH₂CH₂), 0.87 (t, 3H, CH₃(CH₂)₅).

Example 7

| R₁ | R₂ | R₃ | R₄ |
|----|----|----|----|
| H | Methyl (R isomer) | H | n-hexyl |

Flash chromatography:ether:petrol ether=2:3; $R_f$=0.29 (ether:petrol ether=2:3); ¹H-NMR (CDCl₃): 7.16 (d, 2H, H-C2 and H-C6, J=8.5 Hz), 7.07 (d, 2H, H-C3 and H-C5, J=8.5 Hz), 5.33 (br s, 1H, NH), 4.23 (m, 1H, CH(CH₃)CH₂Cl), 3.65 (dd, 1H, CH₂C, J=4.5 and J=11.0 Hz), 3.53 (dd, 1H, CH₂C, J=3.5 and J=11.0 Hz), 2.52 (t, 2H, CH₃(CH₂)₄CH₂, J=7.5 Hz), 1.50–1.60 (m, 2H, CH₃(CH₂)₃CH₂CH₂), 1.28 (m, 6H, CH₃(CH₂)₃CH₂CH₂), 1.19 (d, 3H, CH(CH₃)CH₂Cl, J=6.7 Hz), 0.87 (t, 3H, CH₃(CH₂)₅, J=6.5 Hz).

Example 8

| R₁ | R₂ | R₃ | R₄ |
|----|----|----|----|
| H | Methyl (R isomer) | H | Cyclohexyl |

Flash chromatography:ether:petrol ether=1:1; ¹H-NMR (CDCl₃): 7.16 (d, 2H, H-C2 and H-C6, J=8.4 Hz), 7.11 (d, 2H, H-C3 and H-C5, J=8.4 Hz), 4.24 (m, 1H, CH(CH₃)CH₂Cl), 3.66 (dd, 1H, CH₂Cl, J=4.2 and J=11.0 Hz), 3.54 (dd, 1H, CH₂Cl, J=3.4 and J=11.0 Hz), 2.43 (m, 1H, CH-Ph), 1.70–1.90 (m, 6H, H-cyclohexyl), 1.35–1.45 (m, 4H, H-cyclohexyl), 1.20 (d, 3H, CH(CH₃)CH₂Cl, J=6.7 Hz).

Example 9

| R₁ | R₂ | R₃ | R₄ |
|----|----|----|----|
| H | Methyl (S isomer) | H | cyclohexyl |

Flash chromatography:ether:petrol ether 1:1; $R_f$=0.24 (ether:petrol ether=1:1); ¹H-NMR (CDCl₃): 7.18 (d, 2H, H-C2 and H-C6, J=8.7 Hz), 7.14 (d, 2H, H-C3 and H-C5, J=8.7 Hz), 4.27 (m, 1H, CH(CH₃)CH₂Cl), 3.71 (dd, 1H, CH₂Cl, J=4.4 and J=11.0 Hz), 3.56 (dd, 1H, CH₂Cl, J=3.2 and J=11.0 Hz), 2.45 (m, 1H, CH-Ph), 1.70–1.85 (m, 6H, H-cyclohexyl), 1.36 (m, 4H, H-cyclohexyl), 1.23 (d, 3H, CH(CH₃)CH₂Cl, J=6.8 Hz).

Example 10

| R₁ | R₂ | R₃ | R₄ |
|----|----|----|----|
| H | -ethyl (R isomer) | H | n-hexyl |

Flash chromatography:ether:petrol ether=10:11; $R_f$ =0.38 (ether:petrol ether=1:1); ¹H-NMR (CDCl₃); 7.17 (d, 2H, H-C2 and H-C6, J=8.4 Hz), 7.08 (d, 2H, H-C3 and H-C5, J=8.4 Hz), 5.24 (br s, 1H, NH), 4.02 (m, 1H, CH(CH₂CH₃)CH₂Cl), 3.69 (dd, 1H, CH₂Cl, J=4.0 and 11.0 Hz), 3.60 (dd, 1H, CH₂Cl, J=3.3 and 11.0 Hz), 2.53 (t, 2H, CH₂Ph, J=7.8 Hz), 1.56 (m, 4H, CH₃(CH₂)₃CH₂CH₂ and CH(CH₂CH₃)CH₂Cl), 1.28 (m, 6H, CH₃(CH₂)₃CH₂CH₂), 0.89 (2t, 6H, CH₃(CH₂)₅ and CH(CH₂CH₃)CH₂Cl, J=6.5 and 7.4 Hz).

Example 11

| R₁ | R₂ | R₃ | R₄ |
|----|----|----|----|
| H | -ethyl (R isomer) | H | n-hexyl |

-continued

| R₁ | R₂ | R₃ | R₄ |
|----|----|----|----|

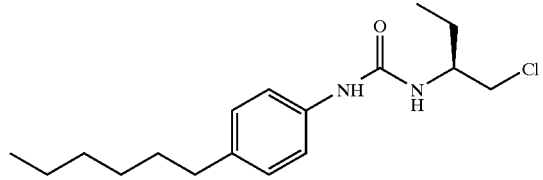

Flash chromatography:ether:petrol ether=35:65; $R_f$=0.28 (ether:petrol ether=2:3); ¹H-NMR (CDCl₃): 7.16 (d, 2H, H-C2 and H-C6, J=8.2 Hz), 7.06 (d, 2H, H-C3 and H-C5, J=8.2 Hz), 5.41 (br s, 1H, NH), 4.02 (m, 1H, CH(CH₂CH₃)CH₂Cl), 3.67 (dd, 1H, CH₂Cl, J=4.2 and 11.0 Hz), 3.58 (dd, 1H, CH₂Cl, J=3.5 and 11.0 Hz), 2.52 (t, 2H, CH₂Ph, J=7.7 Hz), 1.55 (m, 4H, CH₃(CH₂)₃CH₂CH₂ and CH(CH₂CH₃)CH₂Cl), 1.28 (m, 6H, CH₃(CH₂)₃CH₂CH₂), 0.89 (2t, 6H, CH₃(CH₂)₅ and CH(CH₂CH₃)CH₂Cl, J=6.6 and 7.5 Hz).

Example 12

| R₁ | R₂ | R₃ | R₄ |
|----|----|----|----|
| H | Ethyl (S isomer) | H | cyclohexyl |

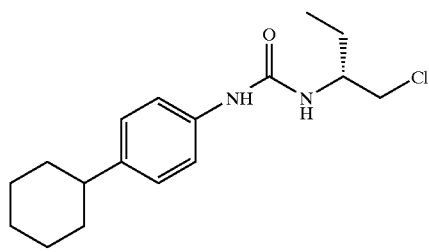

Flash chromatography:ether:petrol ether=10:11; $R_f$=0.38 (ether:petrol ether=1:1); ¹H-NMR (CDCl₃): 7.18 (d, 2H, H-C2 and H-C6, J=8.7 Hz), 7.14 (d, 2H, H-C3 and H-C5, J=8.7 Hz), 4.04 (m, 1H, CH(CH₃)CH₂Cl), 3.73 (dd, 1H, CH₂Cl, J=4.0 and J=11.2 Hz), 3.63 (dd, 1H, CH₂Cl, J=3.2 and J=11.2 Hz), 2.46 (m, 1H, CH-Ph), 1.70–1.85 (m, 4H, H-cyclohexyl), 1.58 (m, 2H, CH(CH₂CH₃)CH₂Cl), 1.18–1.45 (m, 6H, H-cyclohexyl), 0.93 (t, 3H, CH(CH₂CH₃)CH₂Cl, J=7.4 Hz).

Example 13

| R₁ | R₂ | R₃ | R₄ |
|----|----|----|----|
| H | Ethyl (R isomer) | H | cyclohexyl |

-continued

| R₁ | R₂ | R₃ | R₄ |
|----|----|----|----|

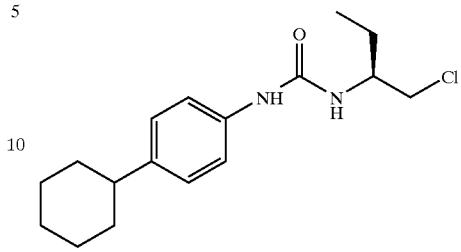

Flash chromatography:ether:petrol ether=1:1; $R_f$=0.35 (ether:petrol ether=1:1); ¹H-NMR (CDCl₃): 7.18 (d, 2H, H-C2 and C6, J=8.5 Hz), 7.13 (d, 2H, H-C3 and H-C5, J=8.5 Hz), 4.03 (m, 1H, CH(CH₃)CH₂Cl), 3.72 (dd, 1H, CH₂Cl, J=3.9 and J=11.1 Hz), 3.64 (dd, 1H, CH₂Cl, J=3.4 and J=11.1 Hz), 2.45 (m, 1H, CH-Ph), 1.65–1.95 (m, 4H, H-cyclohexyl), 1.56 (m, 2H, CH(CH₂CH₃)CH₂Cl), 1.20–1.40 (m, 6H, H-cyclohexyl), 0.93 (t, 3H, CH(CH₂CH₃)CH₂Cl, J=7.4 Hz).

Example 14

| R₁ | R₂ | R₃ | R₄ |
|----|----|----|----|
| H | Propyl (mixture of R and S isomers) | H | n-hexyl |

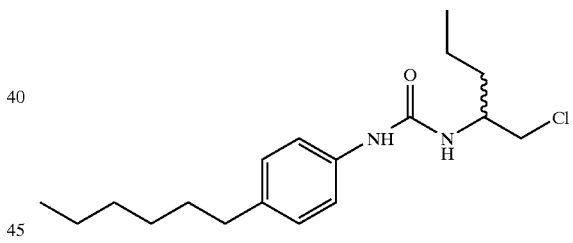

Flash chromatography:ether:petrol ether=2:3; $R_f$=0.31 (ether:petrol ether=2:3); ¹H-NMR (CDCl₃): 7.17 (d, 2H, H-C2 et C6, J=8.2 Hz), 7.04 (d, 2H, H-C3 et C5, J=8.2 Hz), 4.05 (m, 1H, CH(CH₂CH₂CH₃)CH₂Cl), 3.64 (dd, 1H, CH₂Cl, J=4.3 et J=11 Hz), 3.54 (dd, 1H, CH₂Cl, J=3.7 et J=11 Hz), 2.51 (t, 2H, CH₃(CH₂)₄CH₂, J=7.7 Hz), 1.25–1.60 (m, 12H, CH₃(CH₂)₄CH₂ and CH(CH₂CH₂CH₃)CH₂Cl), 0.88 (t, 3H, CH(CH₂CH₂CH₃)CH₂Cl, J=7.2 Hz).

Example 15

| R₁ | R₂ | R₃ | R₄ |
|----|----|----|----|
| H | Propyl (mixture of R and S isomers) | H | cyclohexyl |

-continued

| $R_1$ | $R_2$ | | $R_3$ | $R_4$ |
|---|---|---|---|---|

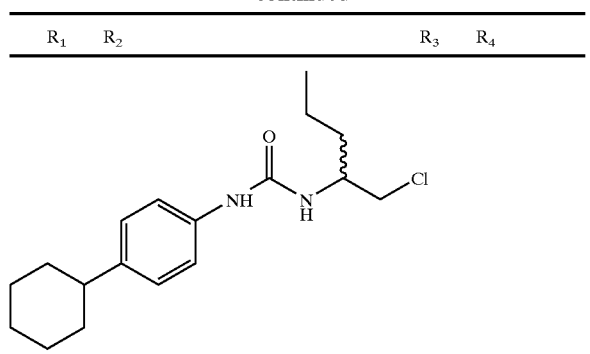

$^1$H-NMR (CDCl$_3$): 7.18 (d, 2H, H-C2 et C6, J=8.7 Hz), 7.13 (d, 2H, H-C3 et C5, J=8.7 Hz), 4.13 (m, 1H, CH(CH$_2$CH$_2$CH$_3$)CH$_2$Cl), 3.73 (dd, 1H, CH$_2$Cl, J=4.1 et J=11.1 Hz), 3.59 (dd, 1H, CH$_2$Cl, J=3.5 et J=11.1 Hz), 2.45 (m, 1H, CH-Ph), 1.20–2.00 (m, 14H, CH$_2$-cyclohexyl et CH(CH$_2$CH$_2$CH$_3$)CH$_2$Cl), 0.91 (t, 3H, CH(CH$_2$CH$_2$CH$_3$) CH$_2$Cl, J=7.1 Hz).

Example 16

Evaluation of Cytotoxycity Activity

Cell culture. Tumor cell lines (B16-F0, Caco-2, DU-145, HT-29, MDA-MB-231 and other cell lines described so far in the patent application) were obtained from the American Type Culture Collection (ATCC HTB-26; Bethesda, Md.). Cells were grown in RPMI 1640 medium supplemented with 10% fetal bovine serum (Hyclone, Road Logan, Utah) and were cultured in a humidified atmosphere at 37° C. in 5% CO$_2$.

Drugs: All drugs were dissolved in DMSO and the final concentration of DMSO in the culture medium was maintained at 0.5% (v/v).

Cytotoxiciy assays. At day-1, tumor cells in suspension in 100 µl were plated in microtiter plates (96 wells). On day-0, tumor cells were treated by addition of escalating concentrations of the drug (100 µl solution). On that day, the number of living cells was determined in wells that were untreated. This was performed in order to be able to evaluate the toxic concentration of the drug needed to kill 50% of the cellular population present at the beginning of the experiments. This value is represented by C$_{50}$ in the table. At day-3, the number of living cells is determined using either MTT or resazurin assays. Growth inhibition activity of these compounds was expressed as the concentration of CAU inhibiting cell growth by 50% G$_{50}$ in the following table The MTT assay was as described above in Example 1. The Resazurin assay was performed as follows:

Aspirate the supernatant (cell suspension: centrifuge first)

Add 100 µL NaCl 0.9% (saline)

Aspirate the supernatant (cell suspension: centrifuge first)

Add 50 µL RZ (resazurin 125 µg/ml/PBS: RPMI without FBS; 1:4) Incubate at 37° C.

Collect fluorescence data at different time.

| FILTER | EM | EM |
|---|---|---|
| CENTER | 590 | 590 |

TABLE V

IN-VITRO CYTOTOXIC ACTIVITY

| Cell line | $R_1$ | $R_2$ | $R_3$ | $R_4$ | $C_{50}$ (µM) | $G_{50}$ (µM) | $C_{50}/G_{50}$ |
|---|---|---|---|---|---|---|---|
| HT-29 | H | Methyl (R isomer) | H | n-hexyl | 12.8 | 5.1 | 2.51 |
| DU-145 | idem | idem | Idem | Idem | 11.8 | 6.3 | 1.86 |
| MDA-MB-231 | idem | idem | Idem | Idem | 31.9 | 11.7 | 2.72 |
| Caco-2 | idem | idem | Idem | Idem | 21.1 | 12.6 | 1.68 |
| B16-F0 | idem | idem | Idem | Idem | 18.2 | 16.3 | 1.12 |
| DU-145 | H | Methyl (S isomer) | H | n-hexyl | 39.5 | 18.9 | 2.09 |
| B16-F0 | idem | idem | idem | Idem | 31.3 | 26.3 | 1.19 |
| MDA-MB-231 | idem | idem | idem | Idem | 43.3 | 31.5 | 1.37 |
| HT-29 | idem | idem | idem | Idem | 44.5 | 32.3 | 1.38 |
| Caco-2 | idem | idem | idem | Idem | 44.2 | 35.8 | 1.23 |
| HT-29 | H | propyl (racemic mixture) | H | n-hexyl | 20.3 | 10.7 | 1.90 |
| DU-145 | idem | idem | idem | Idem | 19.6 | 10.9 | 1.80 |
| Caco-2 | idem | idem | idem | Idem | 21.1 | 12.7 | 1.34 |
| B16-F0 | idem | idem | idem | Idem | 21.3 | 15.8 | 1.71 |
| MDA-MB-231 | idem | idem | idem | Idem | 32.3 | 18.9 | 1.71 |
| DU-145 | H | ethyl (S isomer) | H | n-hexyl | 27.2 | 7.4 | 3.68 |
| Caco-2 | idem | idem | Idem | Idem | 13.7 | 10.2 | 1.35 |
| MDA-MB-231 | idem | idem | Idem | Idem | 40.6 | 18 | |
| B16-F0 | idem | idem | Idem | Idem | 24.9 | 18.8 | 1.33 |

TABLE V-continued

IN-VITRO CYTOTOXIC ACTIVITY

| Cell line | $R_1$ | $R_2$ | $R_3$ | $R_4$ | $C_{50}$ ($\mu M$) | $G_{50}$ ($\mu M$) | $C_{50}/G_{50}$ |
|---|---|---|---|---|---|---|---|
| HT-29 | idem | idem | idem | Idem | 36.8 | 20.8 | 1.77 |
| DU-145 | H | ethyl (R isomer) | H | n-hexyl | 15.8 | 4.6 | 3.46 |
| Caco-2 | idem | idem | idem | idem | 10.9 | 7.5 | 1.45 |
| HT-29 | idem | idem | idem | idem | 20.8 | 13.1 | 1.58 |
| B16-F0 | idem | idem | idem | idem | 18.3 | 14.1 | 1.29 |
| MDA-MB-231 | idem | idem | idem | idem | 30.1 | 15.1 | 1.99 |
| DU-145 | H | methyl (S isomer) | H | cyclohexyl | 27.6 | 7.8 | 3.52 |
| Caco-2 | idem | idem | idem | idem | 14.7 | 8.6 | 1.70 |
| B16-F0 | idem | idem | idem | idem | 17.4 | 15.4 | 1.13 |
| HT-29 | idem | idem | idem | idem | 28.1 | 19 | 1.48 |
| MDA-MB-231 | idem | idem | idem | idem | 42.9 | 27.5 | 1.56 |
| DU-145 | H | methyl (R isomer) | H | cyclohexyl | 25.2 | 8.6 | 2.94 |
| Caco-2 | idem | idem | idem | idem | 20.3 | 15.4 | 1.32 |
| HT-29 | idem | idem | idem | idem | 23.9 | 17.1 | 1.40 |
| B16-F0 | idem | idem | idem | idem | 22.1 | 21.8 | 1.01 |
| MDA-MB-231 | idem | idem | idem | idem | 42.3 | 27.6 | 1.53 |
| DU-145 | H | ethyl (S isomer) | H | cyclohexyl | 22.2 | 7.3 | 3.04 |
| Caco-2 | idem | idem | idem | idem | 17.7 | 10 | 1.77 |
| HT-29 | idem | idem | idem | idem | 22.8 | 13.6 | 1.68 |
| B16-F0 | idem | idem | idem | idem | 21.5 | 17.3 | 1.24 |
| MDA-MB-231 | idem | idem | idem | idem | 40.3 | 19.6 | 2.05 |
| DU-145 | H | ethyl (R isomer) | H | cyclohexyl | 16.2 | 6.9 | 2.35 |
| HT-29 | idem | idem | idem | idem | 16.3 | 9.8 | 2.35 |
| Caco-2 | idem | idem | idem | idem | 15.6 | 9.9 | 1.57 |
| B16-F0 | idem | idem | idem | idem | 17.7 | 15.5 | 1.14 |
| MDA-MB-231 | idem | idem | idem | idem | 32.5 | 16.3 | 1.99 |

Examples 17–29

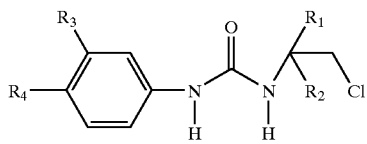

Based on the formula of the compounds of the present invention as shown above, specific molecules were synthesized and later tested for citotoxic activity.

Examples 17

| R1 | R2 | R3 | R4 |
|---|---|---|---|
| H | Methyl (R-isomer) | Methoxy | Methoxy |

-continued

| R1 | R2 | R3 | R4 |
|---|---|---|---|

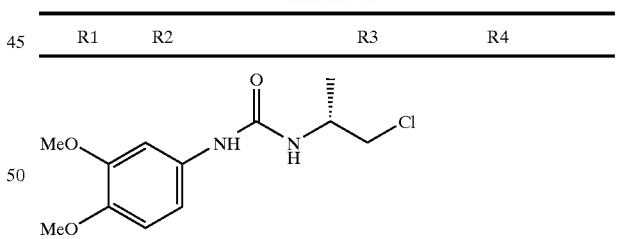

Flash chromatography:9/1:ether/petrol ether; $R_f$=0.31 (100% ether); $^1$H-NMR (CDCl$_3$): 6.95 (d, 1H, H-C2, J=2.2 Hz), 6.72 (d, 1H, H-C5, J=8.4 Hz), 6.64 (dd, 1H, H-C6, J=2.0 and J=8.4 Hz), 4.21 (m, 1H, CH(CH$_3$)CH$_2$Cl), 3.78 (s, 6H, 2 OCH$_3$), 3.67 (dd, 1H, CH$_2$Cl, J=4.1 and J=10.9 Hz), 3.50 (dd, 1H, CH$_2$Cl, J=3.3 and J=10.9 Hz), 1.17 (t, 3H, CH(CH$_3$)CH$_2$Cl, J=6.7 Hz).

Example 18

| R1 | R2 | R3 | R4 |
|---|---|---|---|
| H | Methyl (S-isomer) | Methoxy | Methoxy |

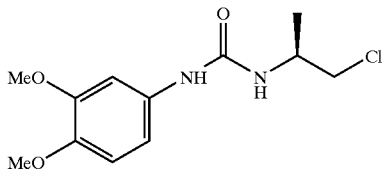

Flash chromatography:9/1:ether/petrol ether; $R_f$=0.33 (100% ether) $^1$H-NMR (CDCl$_3$): 6.96 (d, 1H, H-C2, J=2 Hz), 6.70 (d, 1H, H-C5, J=8.5 Hz), 6.63 (d, 1H, H-C6, J=8.5 Hz), 4.20 (m, 1H, CH(CH$_3$)CH$_2$Cl), 3.76 et 3.78 (2s, 6H, 2 OCH$_3$), 3.65 (dd, 1H, CH$_2$Cl, J=4.2 and J=11.0 Hz), 3.49 (dd, 1H, CH$_2$Cl, J=3.4 and J=11.0 Hz), 1.16 (t, 3H, CH(CH$_3$)CH$_2$Cl, J=6.8 Hz).

Example 19

| R1 | R2 | R3 | R4 |
|---|---|---|---|
| H | Ethyl (S-isomer) | Methoxy | Methoxy |

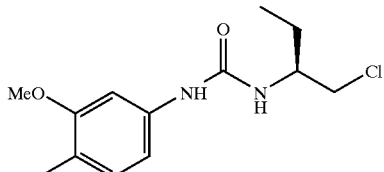

Flash chromatography:7/3:ether petrol ether; $R_f$=0.17 (7/3:ether/petrol ether); $^1$H-NMR (CDCl$_3$): 6.99 (d, 1H, H-C2, J=2.3 Hz), 6.80 (d, 1H, H-C5, J=8.4 Hz), 6.72 (d, 1H, H-C6, J=8.4 Hz), 4.04 (m, 1H, CH(CH$_2$CH$_3$)CH$_2$Cl), 3.85 (s, 6H, 2 OCH$_3$), 3.75 (dd, 1H, CH$_2$Cl, J=3.9 and J=11.2 Hz), 3.63 (dd, 1H, CH$_2$Cl, J=3.3 and J=11.2 Hz), 1.57 (m, 2H, CH(CH$_2$CH$_3$)CH$_2$Cl), 0.93 (t, 3H, CH(CH$_2$CH$_3$)CH$_2$Cl, J=7.5 Hz).

Example 20

| R1 | R2 | R3 | R4 |
|---|---|---|---|
| H | Ethyl (R-isomer) | Methoxy | Methoxy |

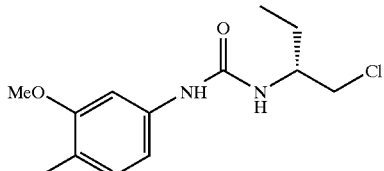

Flash chromatography:7/3:ether/petrol ether; $R_f$=0.17 (7/3:ether/petrol ether); $^1$H-NMR (CDCl$_3$): 7.02 (d, 1H, H-C2, J=2.2 Hz), 6.77 (d, 1H, H-C5, J=8.7 Hz), 6.70 (dd, 1H, H-C6, J=2.2 and J=8.7 Hz), 4.03 (m, 1H, CH(CH$_2$CH$_3$)CH$_2$Cl), 3.83 (s, 6H, 2 OCH$_3$), 3.73 (dd, 1H, CH$_2$Cl, J=4.0 and J=11.2 Hz), 3.61 (dd, 1H, CH$_2$Cl, J=3.2 and J=11.2 Hz), 1.56 (m, 2H, CH(CH$_2$CH$_3$)CH$_2$Cl), 0.92 (t, 3H, CH(CH$_2$CH$_3$)CH$_2$Cl, J=7.4 Hz).

Example 21

| R1 | R2 | R3 | R4 |
|---|---|---|---|
| H | Methyl (R-isomer) | H | n-heptyl |

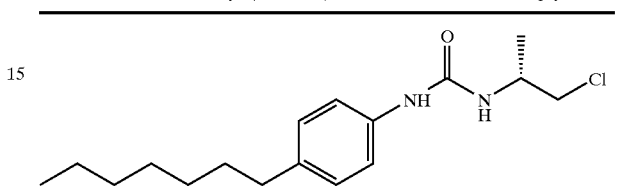

Flash chromatography:35/65 ether/petrol ether; $R_f$=0.16 (2/3:ether/petrol ether); $^1$H-NMR (CDCl$_3$): 7.15 (d, 2H, H-C2 and H-C6, J=8.4 Hz), 7.07 (d, 2H, H-C3 and H-C5, J=8.4 Hz), 4.25 (m, 1H, CH(CH$_3$)CH$_2$Cl), 3.65 (dd, 1H, CH(CH$_3$)CH$_2$Cl, J=4.5 and J=11.0 Hz), 3.53 (dd, 1H, CH(CH$_3$)CH$_2$Cl, J=3.6 and J=11.0 Hz), 2.53 (t, 2H, CH$_3$(CH$_2$)$_5$CH$_2$, J=7.8 Hz), 1.55 (m, 2H, CH$_3$(CH$_2$)$_4$CH$_2$CH$_2$), 1.28 (m, 8H, CH$_3$(CH$_2$)$_4$CH$_2$CH$_2$), 1.20 (d, 3H, CH(CH$_3$)CH$_2$Cl, J=6.7 Hz), 0.87 (t, 3H, CH$_3$(CH$_2$)$_6$, J=6.8 Hz).

Example 22

| R1 | R2 | R3 | R4 |
|---|---|---|---|
| H | Methyl (S-isomer) | H | n-heptyl |

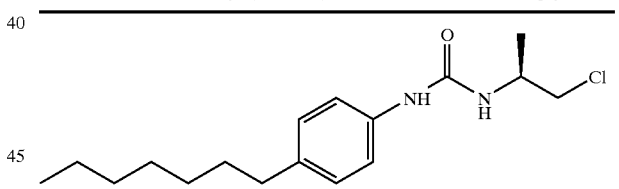

Flash chromatography:4/5/1:CH$_2$Cl$_2$/petrol ether/ether; $R_f$=0.23 (2/3:ether/petrol ether); $^1$H-NMR (CDCl$_3$): 7.16 (d, 2H, H-C2 and H-C6, J=8.3 Hz), 7.07 (d, 2H, H-C3 and H-C5, J=8.3 Hz), 4.23 (m, 1H, CH(CH$_3$)CH$_2$Cl), 3.65 (dd, 1H, CH(CH$_3$)CH$_2$Cl, J=4.5 and J=11.6 Hz), 3.53 (dd, 1H, CH(CH$_3$)CH$_2$Cl, J=3.5 and J=11.0 Hz), 2.52 (t, 2H, CH$_3$(CH$_2$)$_5$CH$_2$, J=7.7 Hz), 1.55 (m, 2H, CH$_3$(CH$_2$)$_4$CH$_2$CH$_2$), 1.28 (m, 8H, CH$_3$(CH$_2$)$_4$CH$_2$CH$_2$), 1.19 (d, 3H, CH(CH$_3$)CH$_2$Cl, J=6.6 Hz), 0.87 (t, 3H, CH$_3$(CH$_2$)$_6$, J=6.6 Hz).

Example 23

| R1 | R2 | R3 | R4 |
|---|---|---|---|
| H | Ethyl (S-isomer) | H | n-heptyl |

-continued

| R1 | R2 | R3 | R4 |
|----|----|----|----|

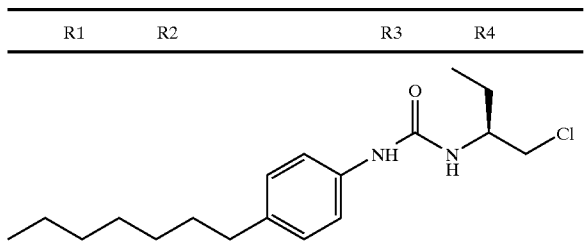

Flash chromatography:4/5/1:CH$_2$Cl$_2$/petrol ether/ether; R$_f$=0.31 (2/3:ether/petrol ether); $^1$H-NMR (CDCl$_3$): 7.17 (d, 2H, H-C2 and H-C6, J=8.2 Hz), 7.09 (d, 2H, H-C3 and H-C5, J=8.2 Hz), 4.03 (m, 1H, CH(CH$_2$CH$_3$)CH$_2$Cl), 3.70 (dd, 1H, CH(CH$_2$CH$_3$)CH$_2$Cl, J=3.7 and J=11.0 Hz), 3.61 (dd, 1H, CH(CH$_2$CH$_3$)CH$_2$Cl, J=3.2 and J=11.0 Hz), 2.53 (t, 2H, CH$_3$(CH$_2$)$_5$CH$_2$, J=7.7 Hz), 1.57 (m, 4H, CH$_3$(CH$_2$)$_4$CH$_2$CH$_2$ and CH(CH$_2$CH$_3$)CH$_2$Cl), 1.27 (m, 8H, CH$_3$(CH$_2$)$_4$CH$_2$CH$_2$), 0.92 and 0.87 (2t, 6H, CH$_3$(CH$_2$)$_6$ and CH(CH$_2$CH$_3$Cl, J=7.6 and J=7.0 Hz).

Example 24

| R1 | R2 | R3 | R4 |
|----|----|----|----|
| H | Ethyl (R-isomer) | H | n-heptyl |

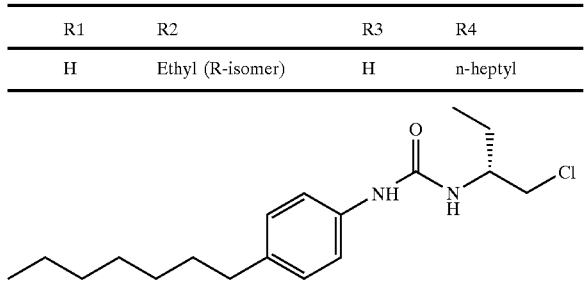

Flash chromatography 4/5/1:CH$_2$Cl$_2$/petrol ether/ether; R$_f$=0.31 (2/3:ether petrol ether) $^1$H-NMR (CDCl$_3$): 7.16 (d, 2H, H-C2 and H-C6 J=8.5 Hz), 7.06 (d, 2H, H-C3 and H-C5, J=8.5 Hz), 4.00 (m, 1H, CH(CH$_2$CH$_3$)CH$_2$Cl), 3.67 (dd, 1H, CH(CH$_2$CH$_3$)CH$_2$Cl, J=4.2 and J=11.1 Hz), 3.58 (dd, 1H, CH(CH$_2$CH$_3$)CH$_2$Cl, J=3.5 and J=11.1 Hz), 2.53 (t, 2H, CH$_3$(CH$_2$)$_5$CH$_2$, J=7.7 Hz), 1.54 (m, 4H, CH$_3$(CH$_2$)$_4$CH$_2$CH$_2$ and CH(CH$_2$CH$_3$)CH$_2$Cl), 1.28 (m, 8H, CH$_3$(CH$_2$)$_4$CH$_2$CH$_2$), 0.91 and 0.87 (2t, 6H, CH$_3$(CH$_2$)6 and CH(CH$_2$CH$_3$)CH$_2$Cl, J=7.4 and J=7.1 Hz).

Examples 25

| R1 | R2 | R3 | R4 |
|----|----|----|----|
| H | Propyl (racemic mixture) | H | cyclohexyl |

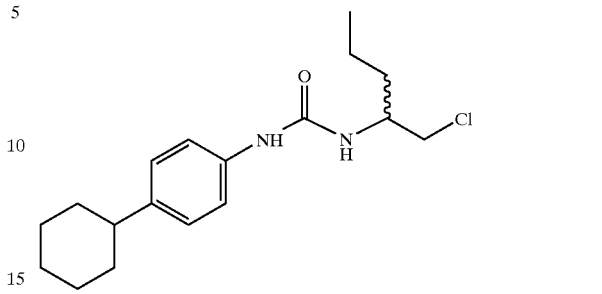

Flash chromatography:2/3ether/petrol ether; R$_f$=0.31 (2/3: ether/petrol ether); $^1$H-NMR (CDCl$_3$): 7.16 (d, 2H, H-C2 and H-C6, J=8.6 Hz), 7.08 (d, 2H, H-C3 and H-C5, J=8.6 Hz), 4.08 (m, 1H, CH(CH$_2$CH$_2$CH$_3$)CH$_2$Cl), 3.66 (dd, 1H, CH$_2$Cl, J=4.2 and J=11.0 Hz), 3.55 (dd, 1H, CH$_2$Cl, J=3.6 and J=11.0 Hz), 2.42 (m, 1H, CH-Ph), 1.70–1.82 (m, 6H, CH(CH$_2$CH$_2$CH$_3$)CH$_2$Cl and H-cyclohexyl), 1.20–1.60 (m, 8H, CH(CH$_2$CH$_2$CH$_3$)CH$_2$Cl and H-cyclohexyl), 0.88 (t, 3H, CH(CH$_2$CH$_2$CH$_3$)CH$_2$Cl, J=7.2 Hz).

Example 26

| R1 | R2 | R3 | R4 |
|----|----|----|----|
| H | Methyl (R-isomer) | H | n-hexyloxy |

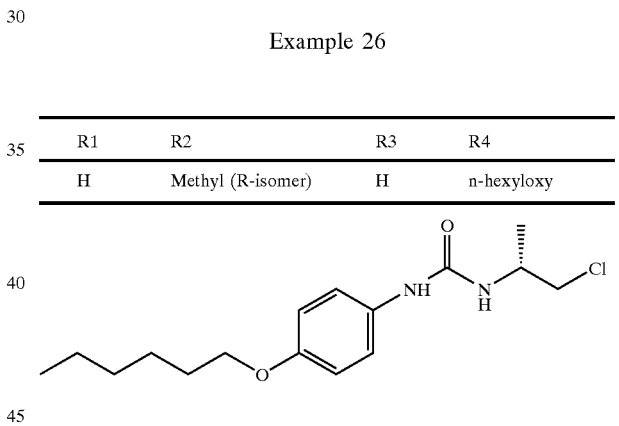

Flash chromatography:1/1:ether/petrol ether; R$_f$=0.16 (1/1:ether/petrol ether); $^1$H-NMR (CDCl$_3$): 7.16 (d, 2H, H-C2 and H-C6, J=8.7 Hz), 6.85 (d, 2H, H-C3 and H-C5, J=8.7 Hz), 4.26 (m, 1H, CH(CH$_3$)CH$_2$Cl), 3.92 (t, 2H, CH$_3$(CH$_2$)4CH$_2$O, J=6.6 Hz), 3.72 (dd, 1H, CH(CH$_3$)CH$_2$Cl, J=4.3 and J=11.0 Hz), 3.55 (dd, 1H, CH(CH$_3$)CH$_2$Cl, J=3.5 and J=11.0 Hz), 1.76 (m, 2H, CH$_3$(CH$_2$)$_3$CH$_2$CH$_2$O), 1.24–1.50 (m, 6H, CH$_3$(CH$_2$)$_3$CH$_2$CH$_2$O), 1.21 (d, 3H, CH(CH$_3$)CH$_2$Cl, J=6.7 Hz), 0.90 (t, 3H, CH$_3$(CH$_2$)$_5$O, J=6.9 Hz).

Example 27

| R1 | R2 | R3 | R4 |
|----|----|----|----|
| H | Methyl (S-isomer) | H | n-hexyloxy |

-continued

| R1 | R2 | R3 | R4 |
|----|----|----|----|

[Chemical structure]

Flash chromatography:55/35/10:$CH_2Cl_2$/petrol ether/ether; $R_f$=0.16 (1/1:ether/petrol ether); $^1$H-NMR ($CDCl_3$): 7.13 (d, 2H, H-C2 and H-C6, J=7.7 Hz), 6.79 (d, 2H, H-C3 and H-C5, J=7.7 Hz), 4.21 (m, 1H, $CH(CH_3)CH_2Cl$), 3.87 (t, 2H, $CH_3(CH_2)_4CH_2O$, J=6.5 Hz), 3.64 (dd, 1H, $CH(CH_3)CH_2Cl$, J=4.5 and J=11.0 Hz), 3.52 (dd, 1H, $CH(CH_3)CH_2Cl$, J=3.5 and J=11.0 Hz), 1.74 (m, 2H, $CH_3(CH_2)_3CH_2CH_2O$), 1.24–1.45 (m, 6H, $CH_3(CH_2)_3CH_2CH_2O$), 1.18 (d, 3H, $CH(CH_3)CH_2Cl$, J=6.6 Hz), 0.89 (m, 3H, $CH_3(CH_2)_5O$).

Example 28

| R1 | R2 | R3 | R4 |
|----|----|----|----|
| H | Ethyl (S-isomer) | H | n-hexyloxy |

[Chemical structure]

Flash chromatography:55/35/10:$CH_2Cl_2$/petrol ether/ether; $R_f$=0.26 (1/1:ether/petrol ether); $^1$H-NMR ($CDCl_3$): 7.16 (d, 2H, H-C2 and C6, J=8.8 Hz), 6.82 (d, 2H, H-C3 and C5, J=8.8 Hz), 4.01 (m, 1H, $CH(CH_3)CH_2Cl$), 3.90 (t, 2H, $CH_3(CH_2)_4CH_2O$, J=6.6 Hz), 3.70 (dd, 1H, $CH(CH_2CH_3)CH_2Cl$, J=4.0 and J=11.2 Hz), 3.60 (dd, 1H, $CH(CH_2CH_3)CH_2Cl$, J=3.3 and J=11.2 Hz), 1.75 (m, 2H, $CH_3(CH_2)_3CH_2CH_2O$), 1.20–1.70 (m, 8H, $CH_3(CH_2)_3CH_2O$) and $CH(CH_2CH_3)CH_2Cl$), 0.90 (2t, 6H, $CH_3(CH_2)_5O$ and $CH(CH_2CH_3)CH_2Cl$, J=7.4 and J=6.5 Hz).

Example 29

Evaluation of Cytotoxycity Activity

Cell culture. Tumor cell lines (B16-F0, Caco-2, DU-145, HT-29, MDA-MB-231 and other cell lines described so far in the patent application) were obtained from the American Type Culture Collection (ATCC HTB-26; Bethesda, Md.). Cells were grown in RPMI 1640 medium supplemented with 10% fetal bovine serum (Hyclone, Road Logan, Utah) and were cultured in a humidified atmosphere at 37° C. in 5% $CO_2$.

Drugs: All drugs were dissolved in DMSO and the final concentration of DMSO in the culture medium was maintained at 0.5% (v/v).

Cytotoxiciy assays. At day-1, tumor cells in suspension in 100 μl were plated in microtiter plates (96 wells). On day-0, tumor cells were treated by addition of escalating concentrations of the drug (100 μl solution). On that day, the number of living cells was determined in wells that were untreated. The number of living cells is determined using either MTT or resazurin assays. Growth inhibition activity of these compounds was expressed as the concentration of CAU inhibiting cell growth by 50% $G_{50}$ in the following table The MTT assay was as described above in Example 1. The Resazurin assay was performed as follows:

Aspirate the supernatant (cell suspension: centrifuge first)

Add 100 μL NaCl 0.9% (saline)

Aspirate the supernatant (cell suspension: centrifuge first)

Add 50 μL RZ (resazurin 125 μg/ml/PBS: RPMI without FBS; 1:4)

Incubate at 37° C.

Collect fluorescence data at different time.

| FILTER | EM | EM |
|--------|-----|-----|
| CENTER | 590 | 590 |

TABLE VI

IN-VITRO CYTOTOXIC ACTIVITY

| Cell line | R1 | R2 | R3 | R4 | G50 (μM) |
|-----------|----|----|----|----|----------|
| B16-F0 | H | Ethyl (R-isomer) | H | n-Heptyl | 3.74 |
| Caco-2 | H | Ethyl (R-isomer) | H | n-Heptyl | 4.85 |
| CHO | H | Ethyl (R-isomer) | H | n-Heptyl | 3.14 |
| DU-145 | H | Ethyl (R-isomer) | H | n-Heptyl | 4.02 |
| HT-29 | H | Ethyl (R-isomer) | H | n-Heptyl | 2.94 |
| K562 | H | Ethyl (R-isomer) | H | n-Heptyl | 2.90 |
| L1210 | H | Ethyl (R-isomer) | H | n-Heptyl | 4.04 |
| MCF-7 | H | Ethyl (R-isomer) | H | n-Heptyl | 3.78 |
| MDA-MB-231 | H | Ethyl (R-isomer) | H | n-Heptyl | 5.17 |
| T24 | H | Ethyl (R-isomer) | H | n-Heptyl | 3.61 |
| B16-F0 | H | Ethyl (R-isomer) | Methoxy | Methoxy | >100 |
| Caco-2 | H | Ethyl (R-isomer) | Methoxy | Methoxy | >100 |
| CHO | H | Ethyl (R-isomer) | Methoxy | Methoxy | >100 |
| DU-145 | H | Ethyl (R-isomer) | Methoxy | Methoxy | >100 |
| HT-29 | H | Ethyl (R-isomer) | Methoxy | Methoxy | >100 |
| K562 | H | Ethyl (R-isomer) | Methoxy | Methoxy | >100 |
| L1210 | H | Ethyl (R-isomer) | Methoxy | Methoxy | >100 |
| MCF-7 | H | Ethyl (R-isomer) | Methoxy | Methoxy | >100 |
| MDA-MB-231 | H | Ethyl (R-isomer) | Methoxy | Methoxy | >100 |
| T24 | H | Ethyl (R-isomer) | Methoxy | Methoxy | >100 |
| B16-F0 | H | Ethyl (S-isomer) | H | n-Heptyl | 4.77 |
| Caco-2 | H | Ethyl (S-isomer) | H | n-Heptyl | 6.32 |
| CHO | H | Ethyl (S-isomer) | H | n-Heptyl | 4.20 |
| DU-145 | H | Ethyl (S-isomer) | H | n-Heptyl | 4.89 |
| HT-29 | H | Ethyl (S-isomer) | H | n-Heptyl | 5.01 |
| K562 | H | Ethyl (S-isomer) | H | n-Heptyl | 3.59 |
| L1210 | H | Ethyl (S-isomer) | H | n-Heptyl | 5.67 |
| MCF-7 | H | Ethyl (S-isomer) | H | n-Heptyl | 4.20 |
| MDA-MB-231 | H | Ethyl (S-isomer) | H | n-Heptyl | 6.12 |
| T24 | H | Ethyl (S-isomer) | H | n-Heptyl | 3.93 |
| B16-F0 | H | Ethyl (S-isomer) | H | n-Hexyloxy | 8.26 |
| Caco-2 | H | Ethyl (S-isomer) | H | n-Hexyloxy | 9.50 |
| CHO | H | Ethyl (S-isomer) | H | n-Hexyloxy | 3.28 |
| DU-145 | H | Ethyl (S-isomer) | H | n-Hexyloxy | 9.46 |
| HT-29 | H | Ethyl (S-isomer) | H | n-Hexyloxy | 8.12 |
| K562 | H | Ethyl (S-isomer) | H | n-Hexyloxy | 3.88 |
| L1210 | H | Ethyl (S-isomer) | H | n-Hexyloxy | 7.42 |
| MCF-7 | H | Ethyl (S-isomer) | H | n-Hexyloxy | 10.41 |
| MDA-MB-231 | H | Ethyl (S-isomer) | H | n-Hexyloxy | 8.75 |
| T24 | H | Ethyl (S-isomer) | H | n-Hexyloxy | 7.16 |
| B16-F0 | H | Ethyl (S-isomer) | Methoxy | Methoxy | >100 |

TABLE VI-continued

IN-VITRO CYTOTOXIC ACTIVITY

| Cell line | R1 | R2 | R3 | R4 | G50 (μM) |
|---|---|---|---|---|---|
| Caco-2 | H | Ethyl (S-isomer) | Methoxy | Methoxy | >100 |
| CHO | H | Ethyl (S-isomer) | Methoxy | Methoxy | >100 |
| DU-145 | H | Ethyl (S-isomer) | Methoxy | Methoxy | >100 |
| HT-29 | H | Ethyl (S-isomer) | Methoxy | Methoxy | >100 |
| K562 | H | Ethyl (S-isomer) | Methoxy | Methoxy | >100 |
| L1210 | H | Ethyl (S-isomer) | Methoxy | Methoxy | >100 |
| MCF-7 | H | Ethyl (S-isomer) | Methoxy | Methoxy | >100 |
| MDA-MB-231 | H | Ethyl (S-isomer) | Methoxy | Methoxy | >100 |
| T24 | H | Ethyl (S-isomer) | Methoxy | Methoxy | >100 |
| B16-F0 | H | H | H | Cyclohexyl | 7.77 |
| Caco-2 | H | H | H | Cyclohexyl | 9.37 |
| CHO | H | H | H | Cyclohexyl | 6.16 |
| DU-145 | H | H | H | Cyclohexyl | 9.09 |
| HT-29 | H | H | H | Cyclohexyl | 8.78 |
| K562 | H | H | H | Cyclohexyl | 7.12 |
| L1210 | H | H | H | Cyclohexyl | 6.94 |
| MCF-7 | H | H | H | Cyclohexyl | 10.73 |
| MDA-MB-231 | H | H | H | Cyclohexyl | 9.17 |
| T24 | H | H | H | Cyclohexyl | 7.57 |
| B16-F0 | H | H | H | n-Heptyl | 5.37 |
| Caco-2 | H | H | H | n-Heptyl | 8.07 |
| CHO | H | H | H | n-Heptyl | 5.39 |
| DU-145 | H | H | H | n-Heptyl | 7.16 |
| HT-29 | H | H | H | n-Heptyl | 4.90 |
| K562 | H | H | H | n-Heptyl | 3.85 |
| L1210 | H | H | H | n-Heptyl | 4.59 |
| MCF-7 | H | H | H | n-Heptyl | 8.62 |
| MDA-MB-231 | H | H | H | n-Heptyl | 7.87 |
| T24 | H | H | H | n-Heptyl | 3.41 |
| B16-F0 | H | H | H | n-Hexyloxy | 5.38 |
| Caco-2 | H | H | H | n-Hexyloxy | 8.42 |
| CHO | H | H | H | n-Hexyloxy | 5.35 |
| DU-145 | H | H | H | n-Hexyloxy | 12.41 |
| HT-29 | H | H | H | n-Hexyloxy | 6.95 |
| K562 | H | H | H | n-Hexyloxy | 5.13 |
| L1210 | H | H | H | n-Hexyloxy | 5.99 |
| MCF-7 | H | H | H | n-Hexyloxy | 9.88 |
| MDA-MB-231 | H | H | H | n-Hexyloxy | 10.18 |
| T24 | H | H | H | n-Hexyloxy | 4.28 |
| B16-F0 | H | H | Methoxy | Methoxy | 35.33 |
| Caco-2 | H | H | Methoxy | Methoxy | >100 |
| CHO | H | H | Methoxy | Methoxy | 33.05 |
| DU-145 | H | H | Methoxy | Methoxy | 48.22 |
| HT-29 | H | H | Methoxy | Methoxy | 18.98 |
| K562 | H | H | Methoxy | Methoxy | 5.14 |
| L1210 | H | H | Methoxy | Methoxy | 19.82 |
| MCF-7 | H | H | Methoxy | Methoxy | 48.97 |
| MDA-MB-231 | H | H | Methoxy | Methoxy | >100 |
| T24 | H | H | Methoxy | Methoxy | 20.59 |
| B16-F0 | H | Methyl (R-isomer) | H | n-Heptyl | 3.79 |
| Caco-2 | H | Methyl (R-isomer) | H | n-Heptyl | 4.94 |
| CHO | H | Methyl (R-isomer) | H | n-Heptyl | 3.46 |
| DU-145 | H | Methyl (R-isomer) | H | n-Heptyl | 3.63 |
| HT-29 | H | Methyl (R-isomer) | H | n-Heptyl | 2.17 |
| K562 | H | Methyl (R-isomer) | H | n-Heptyl | 2.41 |
| L1210 | H | Methyl (R-isomer) | H | n-Heptyl | 2.42 |
| MCF-7 | H | Methyl (R-isomer) | H | n-Heptyl | 3.31 |
| MDA-MB-231 | H | Methyl (R-isomer) | H | n-Heptyl | 4.64 |
| T24 | H | Methyl (R-isomer) | H | n-Heptyl | 2.18 |
| B16-F0 | H | Methyl (R-isomer) | H | n-Hexyloxy | 6.38 |
| Caco-2 | H | Methyl (R-isomer) | H | n-Hexyloxy | 8.57 |
| CHO | H | Methyl (R-isomer) | H | n-Hexyloxy | 2.63 |
| DU-145 | H | Methyl (R-isomer) | H | n-Hexyloxy | 13.24 |
| HT-29 | H | Methyl (R-isomer) | H | n-Hexyloxy | 9.55 |
| K562 | H | Methyl (R-isomer) | H | n-Hexyloxy | 2.68 |
| L1210 | H | Methyl (R-isomer) | H | n-Hexyloxy | 6.21 |
| MCF-7 | H | Methyl (R-isomer) | H | n-Hexyloxy | 8.30 |
| MDA-MB-231 | H | Methyl (R-isomer) | H | n-Hexyloxy | 10.48 |
| T24 | H | Methyl (R-isomer) | H | n-Hexyloxy | 7.14 |
| B16-F0 | H | Methyl (R-isomer) | Methoxy | Methoxy | 26.44 |
| Caco-2 | H | Methyl (R-isomer) | Methoxy | Methoxy | >100 |
| CHO | H | Methyl (R-isomer) | Methoxy | Methoxy | 32.16 |
| DU-145 | H | Methyl (R-isomer) | Methoxy | Methoxy | 34.92 |
| HT-29 | H | Methyl (R-isomer) | Methoxy | Methoxy | 14.76 |
| K562 | H | Methyl (R-isomer) | Methoxy | Methoxy | 9.62 |
| L1210 | H | Methyl (R-isomer) | Methoxy | Methoxy | 10.34 |
| MCF-7 | H | Methyl (R-isomer) | Methoxy | Methoxy | 25.13 |
| MDA-MB-231 | H | Methyl (R-isomer) | Methoxy | Methoxy | 43.58 |
| T24 | H | Methyl (R-isomer) | Methoxy | Methoxy | 12.37 |
| B16-F0 | H | Methyl (S-isomer) | H | n-Heptyl | 6.60 |
| Caco-2 | H | Methyl (S-isomer) | H | n-Heptyl | 7.61 |
| CHO | H | Methyl (S-isomer) | H | n-Heptyl | 3.80 |
| DU-145 | H | Methyl (S-isomer) | H | n-Heptyl | 7.46 |
| HT-29 | H | Methyl (S-isomer) | H | n-Heptyl | 7.69 |
| K562 | H | Methyl (S-isomer) | H | n-Heptyl | 6.96 |
| L1210 | H | Methyl (S-isomer) | H | n-Heptyl | 7.48 |
| MCF-7 | H | Methyl (S-isomer) | H | n-Heptyl | 5.56 |
| MDA-MB-231 | H | Methyl (S-isomer) | H | n-Heptyl | 8.33 |
| T24 | H | Methyl (S-isomer) | H | n-Heptyl | 6.15 |
| B16-F0 | H | Methyl (S-isomer) | H | n-Hexyloxy | 8.45 |
| Caco-2 | H | Methyl (S-isomer) | H | n-Hexyloxy | 7.98 |
| CHO | H | Methyl (S-isomer) | H | n-Hexyloxy | 3.66 |
| DU-145 | H | Methyl (S-isomer) | H | n-Hexyloxy | 12.55 |
| HT-29 | H | Methyl (S-isomer) | H | n-Hexyloxy | 10.50 |
| K562 | H | Methyl (S-isomer) | H | n-Hexyloxy | 7.48 |
| L1210 | H | Methyl (S-isomer) | H | n-Hexyloxy | 8.20 |
| MCF-7 | H | Methyl (S-isomer) | H | n-Hexyloxy | 7.99 |
| MDA-MB-231 | H | Methyl (S-isomer) | H | n-Hexyloxy | 9.08 |
| T24 | H | Methyl (S-isomer) | H | n-Hexyloxy | 9.93 |
| B16-F0 | H | Methyl (S-isomer) | Methoxy | Methoxy | >100 |
| Caco-2 | H | Methyl (S-isomer) | Methoxy | Methoxy | >100 |
| CHO | H | Methyl (S-isomer) | Methoxy | Methoxy | >100 |
| DU-145 | H | Methyl (S-isomer) | Methoxy | Methoxy | >100 |
| HT-29 | H | Methyl (S-isomer) | Methoxy | Methoxy | >100 |
| K562 | H | Methyl (S-isomer) | Methoxy | Methoxy | >100 |
| L1210 | H | Methyl (S-isomer) | Methoxy | Methoxy | >100 |
| MCF-7 | H | Methyl (S-isomer) | Methoxy | Methoxy | >100 |
| MDA-MB-231 | H | Methyl (S-isomer) | Methoxy | Methoxy | >100 |
| T24 | H | Methyl (S-isomer) | Methoxy | Methoxy | >100 |
| B16-F0 | H | Propyl (racemic mixture) | H | Cyclohexyl | 4.14 |
| Caco-2 | H | Propyl (racemic mixture) | H | Cyclohexyl | 6.04 |
| CHO | H | Propyl (racemic mixture) | H | Cyclohexyl | 2.12 |
| DU-145 | H | Propyl (racemic mixture) | H | Cyclohexyl | 4.30 |
| HT-29 | H | Propyl (racemic mixture) | H | Cyclohexyl | 3.03 |
| K562 | H | Propyl (racemic mixture) | H | Cyclohexyl | 4.93 |
| L1210 | H | Propyl (racemic mixture) | H | Cyclohexyl | 4.12 |
| MCF-7 | H | Propyl (racemic mixture) | H | Cyclohexyl | 5.05 |
| MDA-MB-231 | H | Propyl (racemic mixture) | H | Cyclohexyl | 6.37 |
| T24 | H | Propyl (racemic mixture) | H | Cyclohexyl | 4.24 |

Although the invention has been described above with respect with one specific form, it will be evident to a person skilled in the art that it may be modified and refined in various ways. It is therefore wished to have it understood that the present invention should not be limited in scope, except by the terms of the following claims.

I claim:

1. A compound of formula:

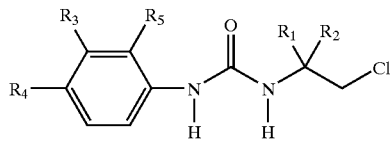

or a prodrug thereof,
wherein
$R_1$ is R-methyl;
$R_2$ is H;
$R_3$ is H;
$R_4$ is iso-propyl; and
$R_5$ is H.

2. A pharmaceutical composition comprising a therapeutically effective amount of the compound of claim 1 and a pharmaceutically acceptable carrier.

3. A medicament for use in treating cancer comprising the compound of claim 1 and a pharmaccutically acceptable carrier.

4. The use of the compound of claim 1 for the treatment of cancer comprising administering a therapeutically effective amount of the compound of claim 1 to a patient in need thereof.

* * * * *